US006171325B1

(12) United States Patent
Mauze et al.

(10) Patent No.: US 6,171,325 B1
(45) Date of Patent: Jan. 9, 2001

(54) APPARATUS AND METHOD FOR INCISING

(76) Inventors: Ganapati R. Mauze, 1114 W. Knickerbocker Dr., Sunnyvale, CA (US) 94087; Michael Greenstein, 860 Covington Rd., Los Altos, CA (US) 94024; Edward D. Verdonk, 1914 Jonathan Ave., San Jose, CA (US) 95125; Paul Lum, 690 Templebar Way, Los Altos, CA (US) 94022

( * ) Notice: Under 35 U.S.C. 154(b), the term of this patent shall be extended for 0 days.

(21) Appl. No.: 09/420,988

(22) Filed: Oct. 20, 1999

Related U.S. Application Data

(62) Division of application No. 09/650,748, filed on Mar. 30, 1998.

(51) Int. Cl.[7] .................................... A61B 17/32
(52) U.S. Cl. ............................ 606/171; 606/181
(58) Field of Search .................... 606/171, 172, 606/177, 178, 181, 182

(56) References Cited

U.S. PATENT DOCUMENTS

| | | | |
|---|---|---|---|
| 4,469,110 | 9/1984 | Slama | 128/770 |
| 4,577,630 | 3/1986 | Nitzsche et al. | 128/314 |
| 4,600,014 | 7/1986 | Beraha | 128/754 |
| 4,712,548 | 12/1987 | Enstrom | 128/314 |
| 4,877,026 | 10/1989 | de Laforcade | 128/305 |
| 5,133,730 | 7/1992 | Biro et al. | 606/182 |
| 5,167,619 | 12/1992 | Wuchinich | 604/22 |
| 5,196,025 | 3/1993 | Ranalletta et al. | 606/182 |
| 5,211,652 | 5/1993 | Derbyshire | 606/182 |
| 5,266,359 | 11/1993 | Spielvogel | 427/388 |
| 5,318,583 | 6/1994 | Rabenau et al. | 606/181 |
| 5,318,584 | 6/1994 | Lange et al. | 606/182 |
| 5,395,387 | 3/1995 | Burns | 606/181 |
| 5,459,325 | 10/1995 | Hueton et al. | 250/458.1 |
| 5,571,132 | 11/1996 | Mawhirt et al. | 606/182 |
| 5,613,978 | 3/1997 | Harding | 606/181 |
| 5,857,983 | 1/1999 | Douglas et al. | 600/538 |

FOREIGN PATENT DOCUMENTS

| | | | |
|---|---|---|---|
| 29800611 U | 1/1998 | (DE) . | |
| WO92/03099 | 3/1992 | (WO) | A61B/17/32 |
| WO96/14799 | 5/1996 | (WO) | A61B/17/32 |
| WO97/28741 | 8/1997 | (WO) | A61B/5/14 |
| WO98/19609 | 5/1998 | (WO) | A61B/17/32 |
| WO99/07295 | 2/1999 | (WO) | A61B/17/14 |

OTHER PUBLICATIONS

Edited by Berardesca, M. D., et al., "Bioengineering of the Skin: Methods and Instrumentation", 1995, pp: 1–13, CRC Press, Boca raton, New York.
Rothman, M. D., "Physiology and Biochemistry of the Skin", pp. 8–25, The University of Chicago Press.
Tregear, "Physiology Interpretation of Skin Impedance Measurements", pp. 600–601, 1965, vol. 205, Nature.
Lawler, et al., "Electrical Characterestics of the Skin, The Impedance of the Surface Sheath and Deep Tissues", pp. 301–308, vol. 34, Journal of Investigative Dermatology.
Cimino, et al., "Physics of Ultrasonic Surgery Using Tissue Fragmentation", pp. 1597–1600, 1995, IEEE Ultrasonics Symposium.
Lal, "Micromachined Silicon Ultrasonic Longitudinal Mode Actuators: Theory . . . ", pp. 129–133, 1996, University of California, Berkeley (A dissertation submitted in partial satisfaction of the requirements for the degree of Doctor of Philosophy).
Letourneau, et al., "Aspiration Biopsy". pp. 8–29, General Considerations.

*Primary Examiner*—Michael Buiz
*Assistant Examiner*—Vy Q. Bui

(57) ABSTRACT

A multi-shaft apparatus for incising a substrate of soft resilient material such as a body tissue. The incising apparatus includes two or more incision shafts each having a distal edge. The shafts are not affixed to each other and are allowed to slide against each other to drive the distal edges alternately against the substrate to incise the substrate. In the case of incising a body tissue, such alternate motion would result in less pain to the patient than a puncture resulting from a sharp jab by a sharp shaft of similar size to the shafts.

16 Claims, 10 Drawing Sheets

APPARATUS AND METHOD FOR INCISING

This is a divisional application of Ser. No. 09/050,748 dated Mar. 30, 1998.

FIELD OF THE INVENTION

The present invention relates to techniques for incising a surface, and more particularly to techniques for incising skin of a patient to obtain a blood sample through a tubular channel.

BACKGROUND

The analysis and quantification of blood components is an important diagnostic tool for better understanding the physical condition of a patient. Since adequate noninvasive blood analysis technology is not currently available, blood samples still need to be obtained by invasive methods from a great number of patients every day and analyzed. A well known example of such needs is self-monitoring of glucose levels by a diabetic individual, e.g., performed at home. Upon doctors' recommendations and using such products, patients typically measure blood glucose level several (3–5) times a day as a way to monitor their success in controlling blood sugar levels. For many diabetics, the failure to test blood glucose regularly may result in damage to tissues and organs, such as kidney failure, blindness, hypertension, and other serious complications. Nevertheless, many diabetics do not measure their blood glucose regularly.

One important reason why patients fail to regularly take blood samples to self-monitor physiological conditions is that the existing monitoring techniques and products for sampling blood cause appreciable pain and discomfort during the sampling process. The current technique of self-administered blood sampling involves using lancets made of stainless steel cylindrical rods the tips of which are shaped to ease penetration into the tissue past the epidermis, into the dermis to rupture the blood vessels in the dermis. Typically, the lancet is propelled by a spring-loaded mechanism that pushes the sharp tip of the lancet into the skin. Studies on pain associated with blood sampling using lancets that are currently commercially available indicate that these lancets often cause considerable pain and large tissue damage. Attempts have been made to reduce pain by reducing the size of the lancet. However, this has not been shown to reduce the amount of pain to an acceptable level for many people.

Therefore, it is desirable to devise techniques of blood extraction and measurement that are easy to administer. There is a need for improved devices and methods for sampling blood that can be used with very little pain and discomfort to the patient.

SUMMARY

In one aspect, this invention provides multiple-shaft apparatuses for incising soft resilient substrates, e.g., body tissue. In an embodiment, the apparatus includes two or more incision shafts each having a distal edge. The shafts are non-fixedly associated with one another for relative motion to drive the distal edges against the body tissue at different velocities to incise the body tissue (hereinafter "tissue").

The main cause of pain in blood sampling is believed to be the propagation of the pressure waves initiated by the impact of the lancet tip on the tissue. All the force needed for penetration is supplied in an instant by the spring in conventional lancet driving mechanisms. The total pressure on the tissue using such spring-loaded impact lancets is therefore large and consequently leads to significant pain. A multiple-shaft proboscis having a channel through which blood can be passed is applicable in an apparatus for drawing blood for sampling from a patient according to the present invention. The different shafts (or parts of the proboscis) cut into the tissue at different times, e.g., by a reciprocative motion as the proboscis is advanced against the tissue. This invention reduces pain associated with sampling blood via a needle-like structure being inserted into the body tissue. The intermittent, "stop and go" motion of the cutting edges of the proboscis helps the cutting edges to cut into the tissue as they are advanced into the tissue. This intermittent cutting results in small penetration steps and very small penetration pressure being applied to the tissue through the pushing action of the proboscis. The intermittent cutting motion is preferably reciprocative, i.e., reciprocating, i.e., with a reverse in direction periodically. The intermittent cutting motion can also be either longitudinal or rotational. Small pressure resulting from such cutting motions effects extremely low stimulation to the nerve endings at the tissue being cut for blood sampling. As a result, very little pain is sensed by the patient in the blood sampling procedures of the present invention.

BRIEF DESCRIPTION OF THE DRAWINGS

The following figures are included to better illustrate the embodiments of the apparatus and technique of the present invention. In these figures, like numerals represent like features in the several views.

DETAILED DESCRIPTION OF THE INVENTION

In one aspect of the invention, the present invention provides an apparatus for incising a surface of a patient to obtain blood, by inserting a multi-shaft proboscis into the body tissue through its surface to obtain a blood sample with relatively little pain. Using the proboscis apparatus, a patient can obtain a blood sample with less pain than utilizing a conventional blood sampling apparatus such as a lancet and associated device.

Figure 1:
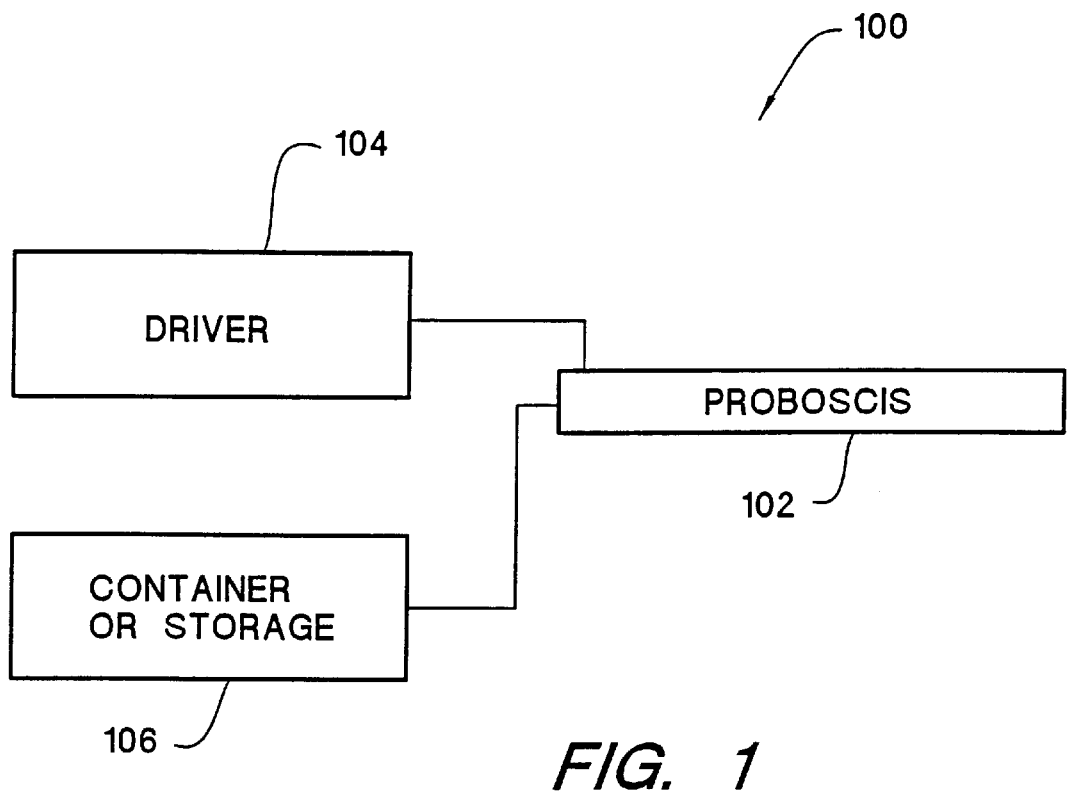
FIG. 1 shows a block diagram of an embodiment of a blood sampling apparatus of the present invention.

FIG. 1 is a block diagram illustration of an embodiment of an blood sampling apparatus of the present invention. In FIG. 1, the blood sampling apparatus 100 has a proboscis 102, which is driven by a driver 104 to incise or cut into body tissue. A container 106, having a space such as a cavity or chamber, can be connected to the proboscis in fluid communication for containing or storing the blood being sampled and passed therein from the proboscis 102. Optionally, capillary action, or suction from a vacuum-creating device, can be used to draw blood from the body tissue.

A. PROBOSCIS

Figure 2A:
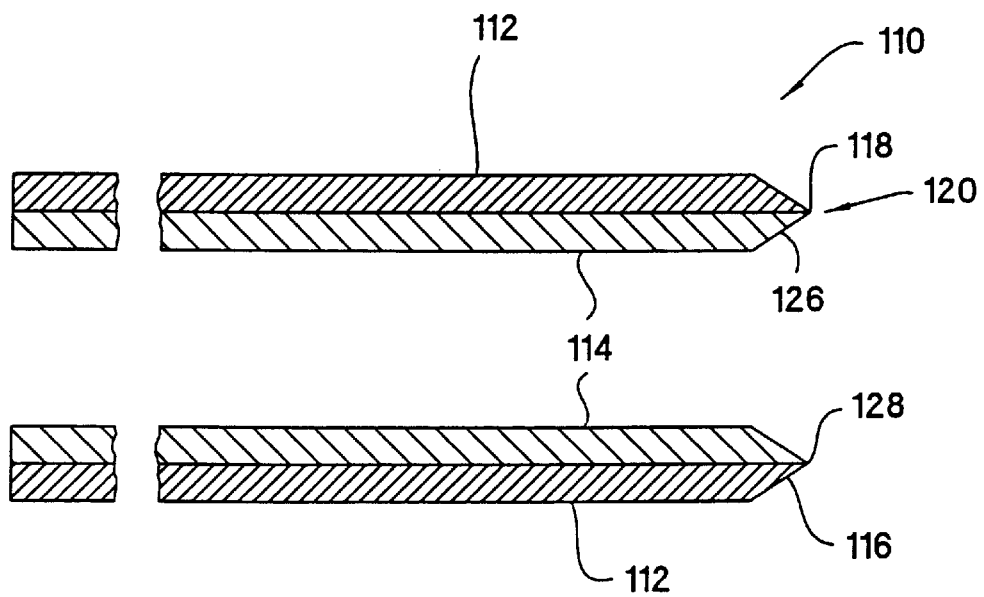
FIG. 2A shows a sectional view of an embodiment of a proboscis of the present invention.
Figure 2B:
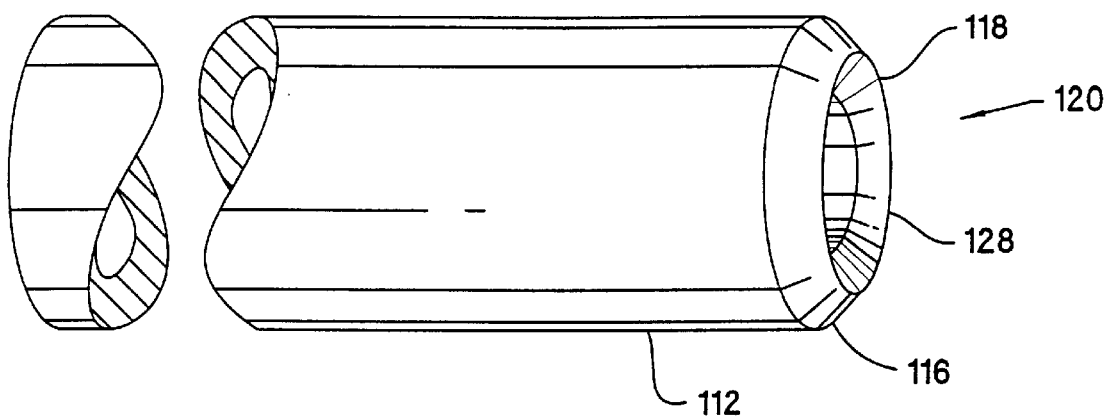
FIG. 2B shows an isometric view in portion of the proboscis of FIG. 2A.

The proboscis of the present invention is constructed to incise, or cut into body tissue with reduced or minimal pain to the patient. As used herein, the term "proboscis" refers to a multiple-part, elongated, needle-like structure with or without a channel wherein a fluid can flow. Such a proboscis can be used for inserting into a soft, resilient material. For example the proboscis can be used to cut into a body tissue such as skin of an individual, to rupture the skin and capillaries below the skin to cause bleeding. If desired, the proboscis can be of a design suitable for drawing a fluid, e.g., blood, from the material through, for example, a channel in the proboscis. FIG. 2A and FIG. 2B illustrate an embodiment of a proboscis of the present invention. In this embodiment, the proboscis 110 contains two shafts 112, 114, which are concentric tubes. As used herein, the tubes can be considered "shafts" since they are elongated and run along the proboscis. The distal end of the outer tube 112 is beveled to result in a bevel surface 116 facing outwardly away from the axis of the tube 112 at an angle. The bevel surface 116 leads to a sharp ring-shaped end 118 at the distal tip 120 of the proboscis 110. As is herein, the term "distal" refers to the position, direction or orientation that is towards the body tissue to be incised. The term "proximal" refers to a position, direction or orientation opposite to that of "distal." The distal end of the inner tube 114 is beveled to result in a bevel surface 126 facing inwardly at an angle towards the axis of the tube 114. The bevel surface 126 leads to a sharp ring-shaped end 128 at the tip 120 of the proboscis 10. The dimensions of the proboscis depend on the amount of blood needed to be drawn. Typically, e.g., in blood sampling for glucose testing self-administered by patients, the proboscis can have a channel about 100 to 2,000 microns in inside diameter, preferably about 200 to 500 microns in inside diameter. The longitudinal reciprocative relative movement between two halves can be measured in microns (e.g., in a range of 1 to 100 microns).

Figure 2C:
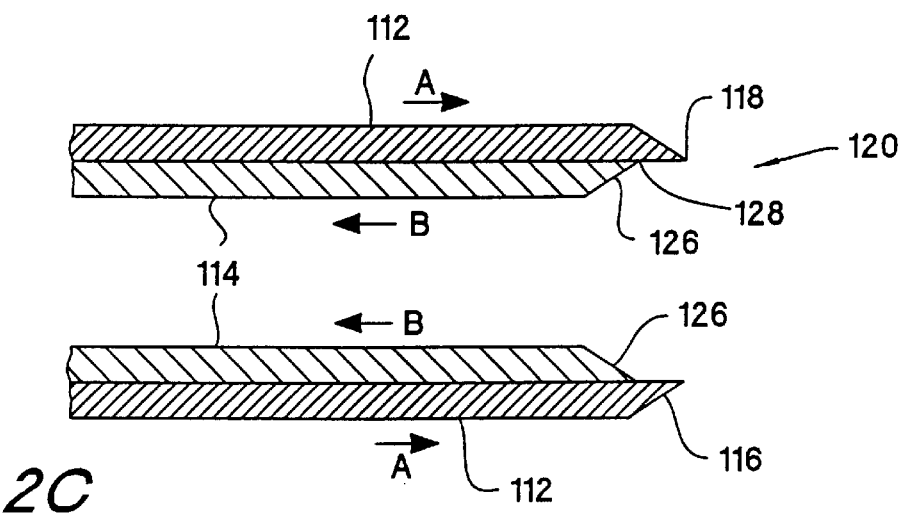
FIGS. 2C–2D are sectional views showing the relative movement of the parts of the proboscis of FIG. 2A according to the present invention.
Figure 2D:
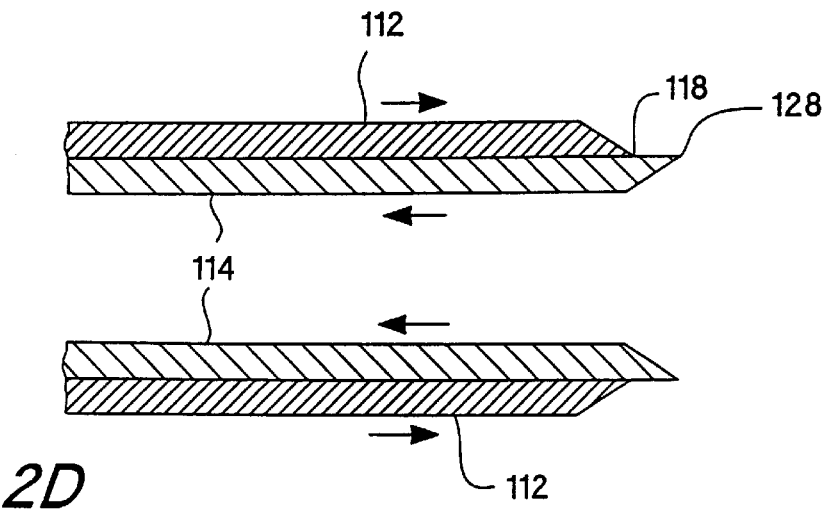

FIG. 2C and FIG. 2D illustrate one way how the proboscis 110 of FIGS. 2A and 2B incises body tissue. The outer tube 112 (or shaft) and inner tube 114 (or shaft) associate with each other in close proximity with low friction between them so that one can slide on the other freely. In the embodiment illustrated in FIGS. 2C and 2D, the tubes 112, 114 are driven to move longitudinally reciprocatively such that alternately the sharp ring-shaped end 118 of the outer tube 112 is more distal than the end 128 of the inner tube 114 (as shown in FIG. 2C) and the sharp ring-shaped end 128 of the inner tube 114 is more distal than the end 118 of the outer tube 112 (as shown in FIG. 2D). The arrows A in FIG. 2C show the direction of the movement of the outer tube 112 towards the distal end and the arrows B shows the direction of the movement of the inner tube 114 away from the distal end. Similarly, the arrows in FIG. 2D show the directions of reciprocative movement in the opposite direction as those of FIG. 2C.

In the embodiment shown in FIGS. 2A–2D, the inner tube 114 is beveled inside and the outer tube 112 is beveled outside. Such a configuration provides a sharp circular contact by the distal tip 120 of the proboscis 110 with the tissue. The static cutting angle of this proboscis 110 is twice the bevel of each edge (i.e., if the bevel angle is the same for the inner tube and the outer tube). Since the inner tube and outer tube are in close contact, no significant gap exists between the tubes 112 and 114. This structure provides a clean cutting edge, substantially eliminating the risk of tissue or blood being trapped between the tubes.

Figure 3:
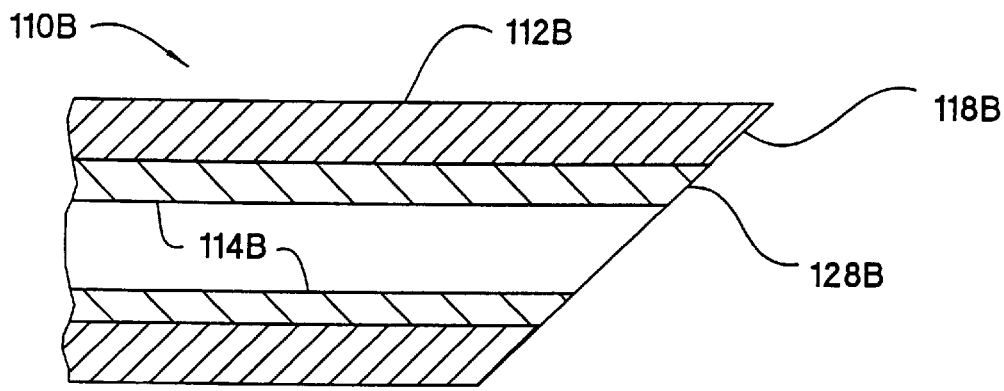
FIG. 3 to FIG. 5 are sectional views showing exemplary embodiments of concentric tubular proboscis according to the present invention.

FIG. 3 shows an embodiment of a proboscis 110B in which both the outer tube 112B and inner tube 114B are shaped at an angle like a hypodermic needle. Thus, when aligned, the angled edge 118B of the outer tube 112 and the angled edge 128B of the inner tube 114B are matched and form the same angle with the axis of the tubes 112B and 114B, which are concentric. An advantage of this structure is that both tubes can be ground at once to form the angled edges 118B and 128B. This proboscis, as one skilled in the art will also understand regarding the following embodiments, can be driven using the reciprocative action as described above for the embodiment of FIGS. 2A–2D.

Figure 4:
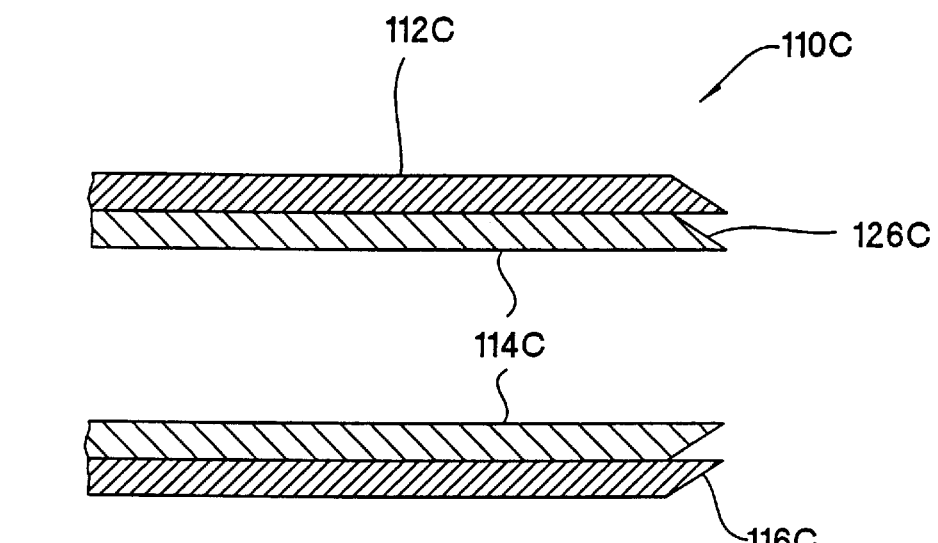

FIG. 4 shows an embodiment of a proboscis 110C in which both the outer tube 112C and inner tube 114C are beveled outwardly at the same angle. When the inner and outer tubes are correctly aligned they can be ground together with the same grind step, since the bevel surface 116C of the outer tube 112C and the bevel surface 126C of the inner tube 114C face the same direction. This structure also provides a good hold on the tissue by one tube when the other cuts or incises the tissue, thereby providing easy penetration into the tissue as the proboscis is being inserted into the tissue with reciprocative action.

Figure 5:
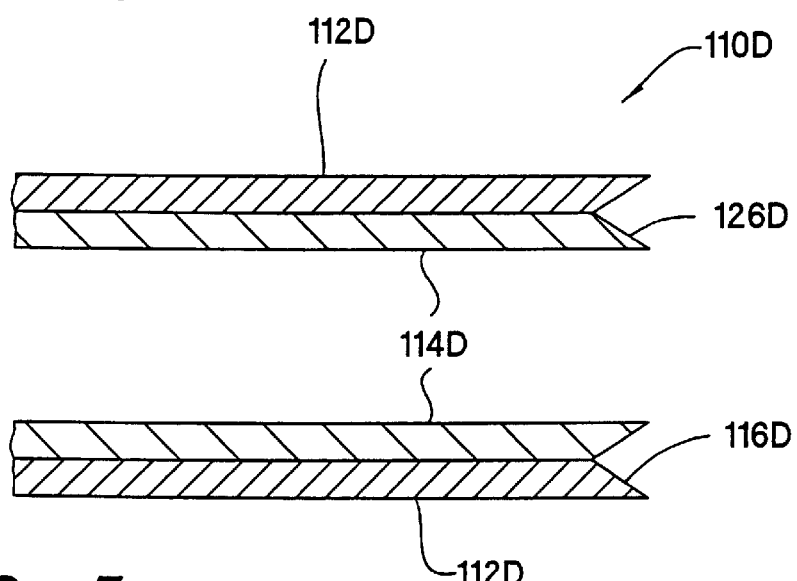

FIG. 5 shows an embodiment of a proboscis 110D in which the outer tube 112D is beveled inwardly towards the axis at an angle and inner tube 114D is beveled outwardly away from the axis at an angle. The bevel surface 116D and 126D of the tubes face generally at an angle towards each other. This structure also provides a good hold on the tissue by one tube when the other cuts or incises the tissue. It is suited for inserting into a capillary bed to sample blood.

Although in the above the cutting devices are described as hollow to facilitate combining the steps of cutting and channeling blood to a storage or measuring device, the cutting and the channeling steps can be done with different devices. In that case the hollow proboscis can be replaced with a non-hollow one, which includes component shafts that reciprocatively move relative one another for cutting. For example, the component shafts can be two halves of a solid needle, in which the two halves slide on each other as they move reciprocatively back and forth longitudinally. It is further contemplated that the proboscis can have two or more parts to form such a solid proboscis. Additionally, the solid pieces of the proboscis can slide inside a tube, which steadies the pieces from lateral motion, i.e., in directions generally perpendicular to the reciprocative movement.

Relative Motion of the Cutting Edges

To facilitate penetration of the shafts into a substrate, i.e., a soft resilient material such as body tissue, e.g., skin, the shafts are preferably driven to cut or incise the substrate at different velocity. As used herein, the term "difference in velocity" or "different velocity" refers to either a difference in either direction of motion or magnitude of speed, or both among the shafts. Such a cutting process will result in the shafts not penetrating the substrate to the same degree simultaneously, thus reducing the pressure waves on the substrate. Thus, incising with the separate parts of the proboscis to insert it into the body tissue according the present invention can be done with reduced pain.

Figure 6:
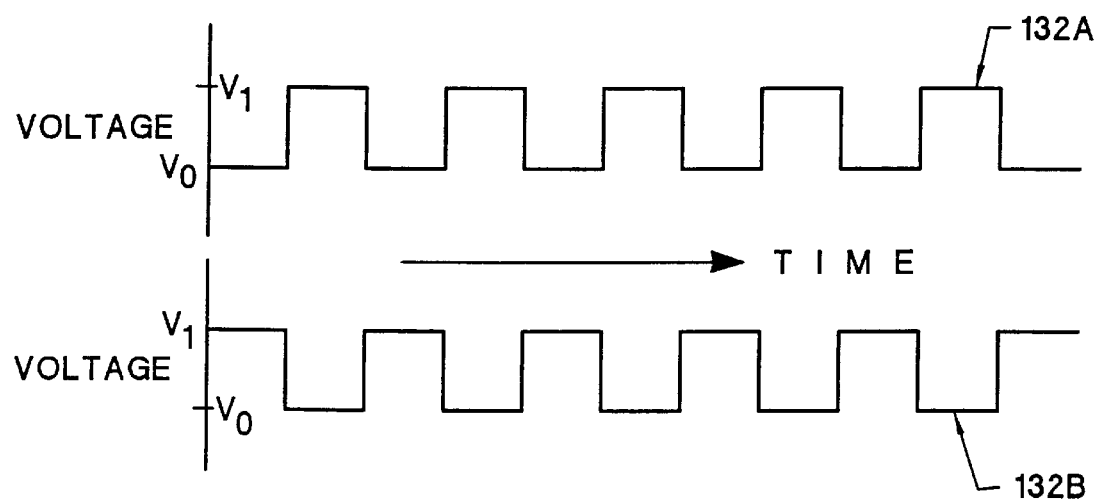
FIG. 6 shows a graphical representation of an example of how the proboscis sections of FIG. 2 can be driven.
Figure 8A:
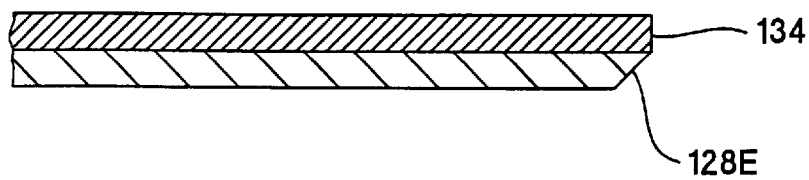
FIG. 8A to FIG. 8D show sectional views of embodiments in which only one tube in the proboscis has a cutting edge.
Figure 8B:
Figure 8C:
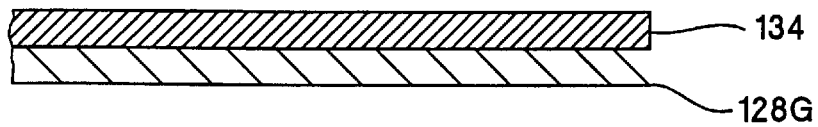
Figure 8D:
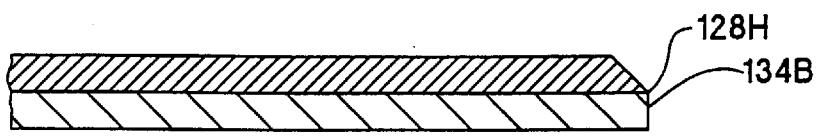

For illustration, FIG. 6 illustrates exemplary reciprocative relative motion of the proboscis parts (e.g., the shafts or tubes of FIGS. 2 to 5). The top tracing 132A represents the voltage of the driver that drives the reciprocative motion of, for example, the inner tube of a proboscis, and the bottom tracing 132B represents the voltage of the driver that drives the reciprocative motion of, for example, the outer tube of the same proboscis. At the lower voltage $V_0$ the tube is stationary and at the higher voltage $V_1$ the tube is driven to cut into the tissue. The incising process can be initiated by pressing the cutting edges of the proboscis against the tissue to be penetrated with a minimal force. One of the cutting edges is then pushed towards the tissue with a small differential force while the other edge is anchoring the tissue. After the moving edge has penetrated into the tissue to a predetermined differential depth, that edge is arrested and it in turn becomes the anchoring edge as the other edge is moved with a differential force. The other edge is moved until it penetrates into the tissue to a predetermined differential depth. The whole process is repeated, with the two cutting edges moving alternately in reciprocative motion. Although the present invention is not limited by any scientific theory, it is believed that pain is reduced as the proboscis is inserted into a patient because the noncontinuous incising process employed in the present invention cuts the tissue in small amounts in a step by applying minimal pressure to the tissue for cutting. It has been shown that the application of reciprocating cutting device reduces the total force required to penetrate a tissue-like material. This reciprocative process reduces the tendency of the cutting edge being bound by friction to the tissue being cut. Thus, in the present invention, the reciprocative motion of the parts of the proboscis reduces the total force transmitted to the tissue and hence reduces the pain associated with cutting. Further, since the two cutting edges do not move at the same time, one cutting edge stabilizes the tissue while the other cutting edge cuts, thereby reducing the pushing and pulling forces transferred to the tissue and hence to the nerves. The reduction of pushing and pulling forces on the nerves results in less pain to the patient. In using the cutting device of the present invention, typically the cutting time is in the range of about 0.1 to 5 seconds, preferably about 0.5 to 1 second. In this way the sharp pain associated with the sudden jab as done in the convention incising methods is reduced.

Figure 7:
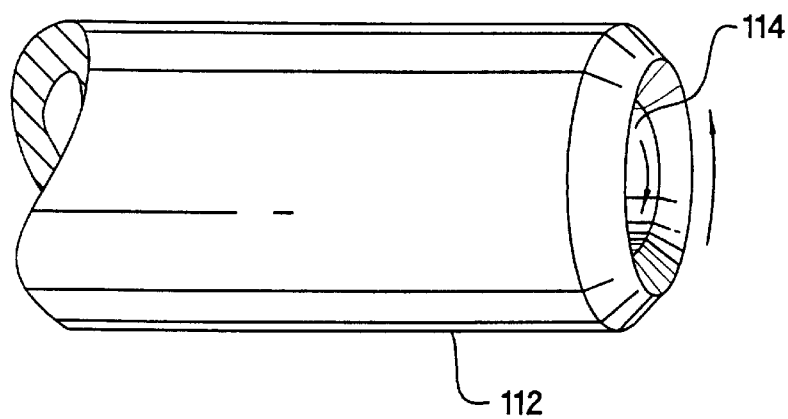
FIG. 7 shows an isometric view in portion of an embodiment of a proboscis for rotational cutting motion according to the present invention.

One skilled in the art will be able to vary the above described procedure in a variety of ways. For example, the distance, speed, and timing of the reciprocative motion can be varied. Another example is illustrated in FIG. 7, in which the reciprocative relative motion of the inner tube and outer tube of a structure similar to that of FIG. 2 is rotational instead of longitudinal. When rotation is used to cut the tissue, preferably, one of the tubes is held static while the other rotates, resulting in a shearing action for cutting the tissue without applying a substantial impact force. Thus, one cutting edge cuts the tissue by a curving, slicing motion of the cutting edge while the other cutting edge stationarily anchors the tissue and vice versa as the process is reversed so the tubes alternately cut into the tissue. Such a reduced impact cutting method considerably reduces the pressure waves, which are associated with pain, transmitted to the tissue. As another exemplary alternative, instead of driving the tubes to move in opposite directions, the tubes can be driven to move in the same direction. Also, instead of driving each tube to move back and forth, the same tube can be driven to move always in the same direction. In the case the tubes move in opposite directions, the tubes can be driven to move simultaneously as well.

In the above described embodiments, both of the proboscis parts (which include cutting edges) are moved to cut into the tissue as the proboscis is urged into the tissue. However, embodiments of proboscis can be used in which only one of the proboscis parts is moved for cutting. FIGS. 8A to 8D illustrate exemplary embodiments of such a proboscis. One of the tubes can have a blunt distal edge 134, or 134B for holding on to the tissue as the other edge 128E, 128F, 128G, or 128H moves.

Generally, the distance of travel of a proboscis part for each reciprocative (or regular intermittent) movement is selected to reduce the pressure wave on the skin so as to reduce the pain associated with sampling blood. Although the present invention is not limited to any specific values, typically, the distance of travel of a shaft in each reciprocative movement for a proboscis section is about 0.001 mm to 0.5 mm, preferably about 0.01 mm to 0.1 mm. The frequency of reciprocative (or reaular intermittent) movement is typically about 0.1 KHz to 100 KHz, preferably about 10 KHz to 75 KHz.

Split Proboscis

Figure 9A:
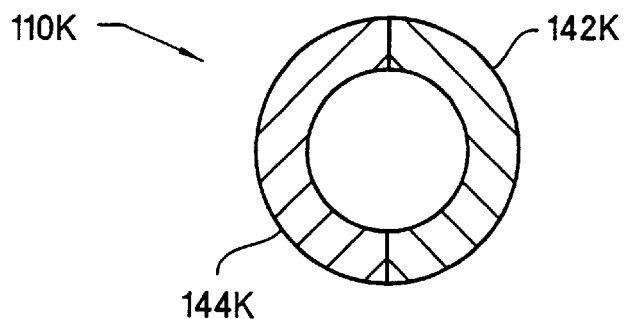
FIG. 9A shows a sectional view of an embodiment of a proboscis that is split in halves longitudinally.
Figure 9B:
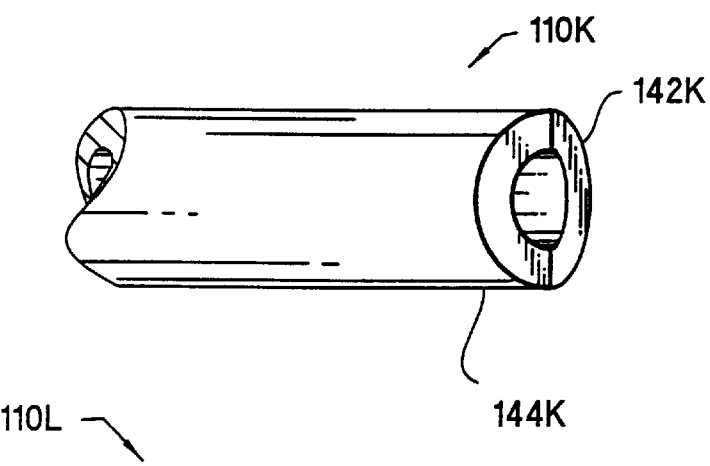
FIG. 9B shows an isometric view in portion of the proboscis of FIG. 9A.
Figure 10:
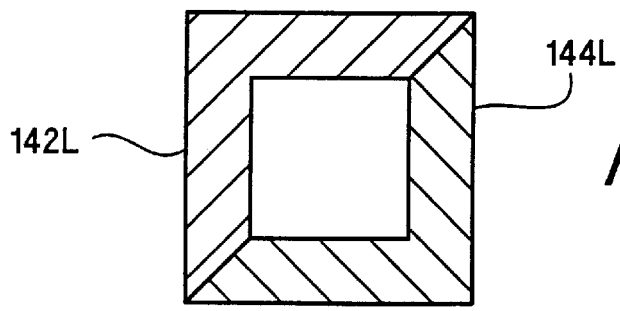
FIG. 10 to FIG. 14 show sectional views of embodiments of a proboscis composed of longitudinal sections forming a channel.
Figure 11:
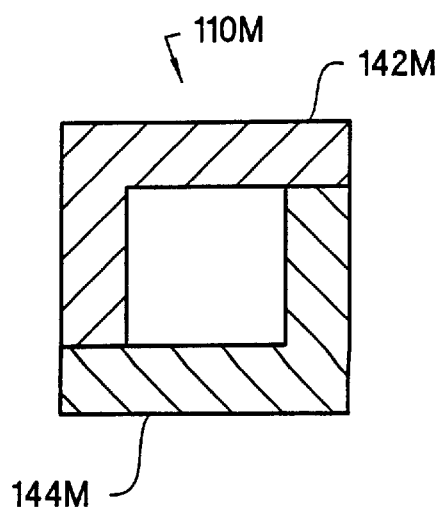
Figure 12:
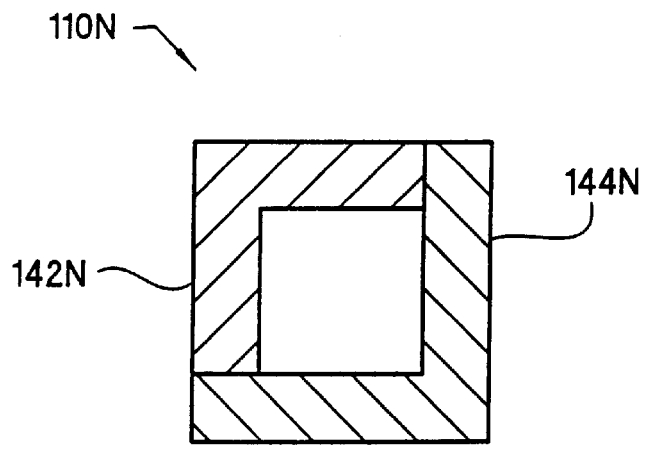
Figure 13:
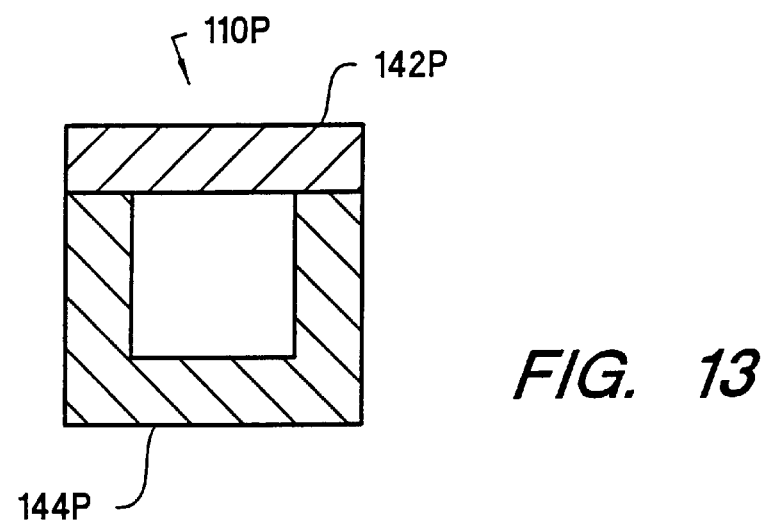

As an alternative to using concentric tubes for reciprocative cutting, one can use a proboscis that contains parts that match with one another to form a channel through which fluid can flow. Thus, a tube is split into two or more longitudinal sections (i.e., pieces), which can be considered as shafts, each of which sections reciprocates with respect to the other. FIGS. 9 to 14 illustrates exemplary embodiments of proboscis in which two or more pieces join to form a channel. The cutting edges of the proboscis sections may be prepared in various combinations of those shown in the above-described embodiments for the concentric tubes. Furthermore, one of the split sections can be structured for anchoring and the other can be structured with a cutting edge for cutting. FIGS. 9A and 9B illustrates an embodiment of a proboscis 110K, with two longitudinal halves 142K, 144K each with a semicircular cross-section, in the form of a cylindrical capillary tube as a whole. The distal end of each of the halves 142K, 144K is beveled to result in a distal sharp cutting edge. FIG. 10 shows a split proboscis embodiment with two halves 142L and 144L forming a proboscis 110L with a square cross section.

Figure 14:
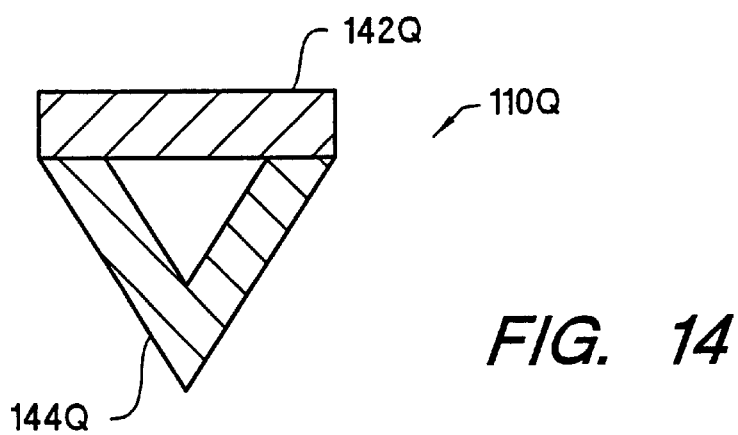

Various ways can be used to split the proboscis to result in a channel of a particular shape. For example, for a square channel, the proboscis can be split in, e.g., the ways illustrated in FIGS. 10 to 13. In these figures, the proboscis 110L–110P are composed of sections 142L–142P and sections 144L–144P respectively for the different embodiments. Similarly, for a proboscis embodiment 110Q with a channel having a triangular cross-section and composed of sections 142Q and 144Q (for example, as shown in FIG. 14), the sections can be structured with sections having many different shapes.

B. DRIVING MECHANISM

The proboscis sections of the present invention can be driven reciprocatively by a variety of mechanisms, including, e.g., electromagnetic, electrostatic, pneumatic, hydraulic, and piezoelectric mechanisms. For illustrative purposes, exemplary embodiments of piezoelectric mechanisms for driving proboscis sections are described below.

Figure 15:
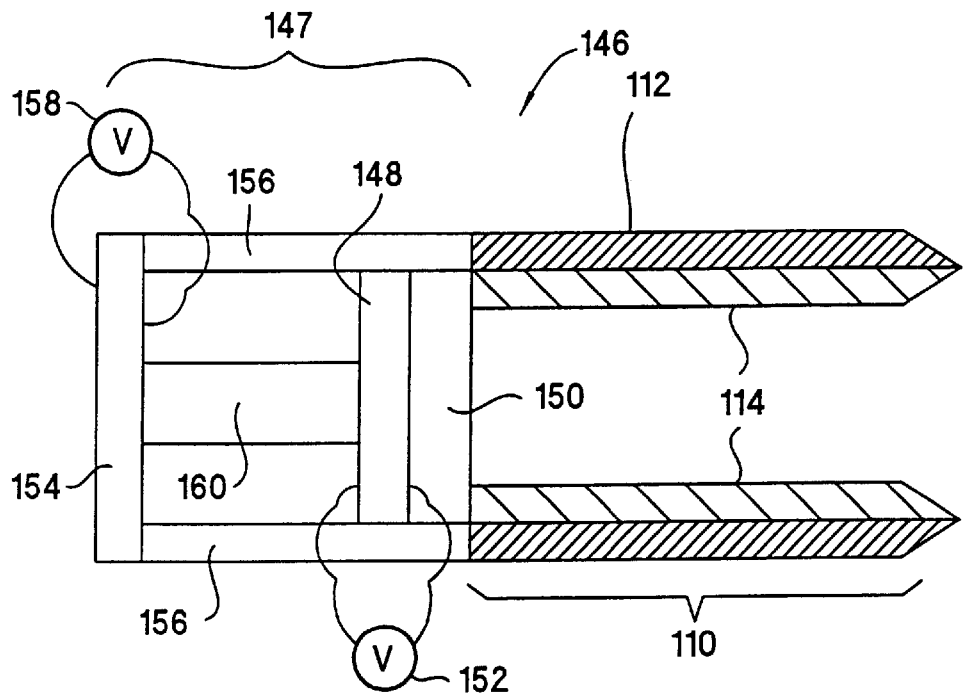
FIG. 15 shows a schematic sectional representation of an embodiment of blood sampling apparatus having a driver.

FIG. 15 shows such an embodiment that is suitable for producing reciprocative motion of the concentric tubes as those described above. The blood sampling apparatus 146 includes proboscis 110 and driver 147. Although one skilled in the art will understand how a suction or storage mechanism can be connected to such an apparatus, no separate suction or storage mechanism is shown in the figure for the sake of clarity. In the driver 147, a first piezoelectric (PZT) device 148 when activated will transfer oscillating motion by means of transfer support 150 to the inner tube 114 of the proboscis 110. The first PZT device 148 is controlled by the first power supply 152. Similarly, a second PZT device 154, controlled by second power supply 158, transfers oscillating motion by means of second transfer support 156 to the outer tube 112 of the proboscis 110. A damper 160 may be used to prevent inter-PZT-device transfer of oscillation. Thus, each PZT device can move and slide in close proximity relative the other without transferring its motion to the other. The power supplies 152 and 158 may be coordinated to result in cyclical, orchestrated motion, for example, as done in FIG. 6. Furthermore, the power supplies can be controlled to varying the velocity of reciprocative motion of the proboscis sections.

Figure 16:
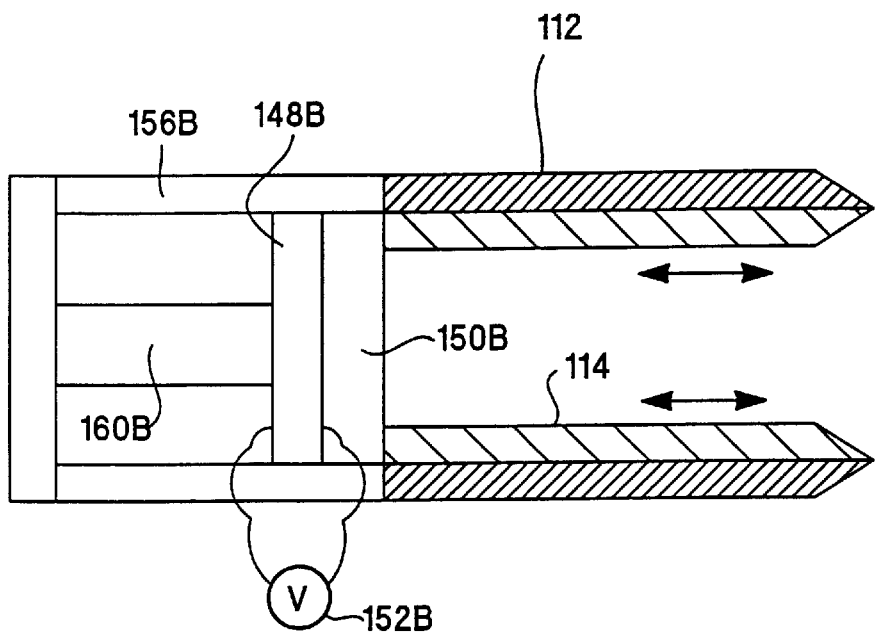
FIG. 16 shows a schematic sectional representation of another embodiment of a blood sampling apparatus having a driver.

FIG. 16 shows an illustrative embodiment of a blood sampling apparatus in which only one tube is moved reciprocatively while the other stays static. As in the apparatus shown in FIG. 15, the PZT device 148B drives the reciprocative motion of the inner tube 114 by transferring the oscillatory forces through the transfer support 150B, whereas the outer tube 112 is static. A damper 160B prevents the transfer of oscillatory motion from the PZT device 148B to the structures, such as support 156B, that are rigidly connected to the outer tube. A power supply 152B provides the power for activating the PZT device 148B to produce the oscillating motion.

Figure 17:
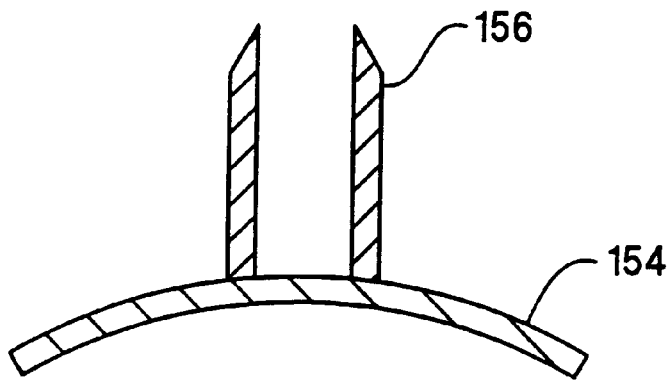
FIG. 17 shows a schematic sectional representation of a proboscis associated with a driver having a curved PZT piece.
Figure 18:
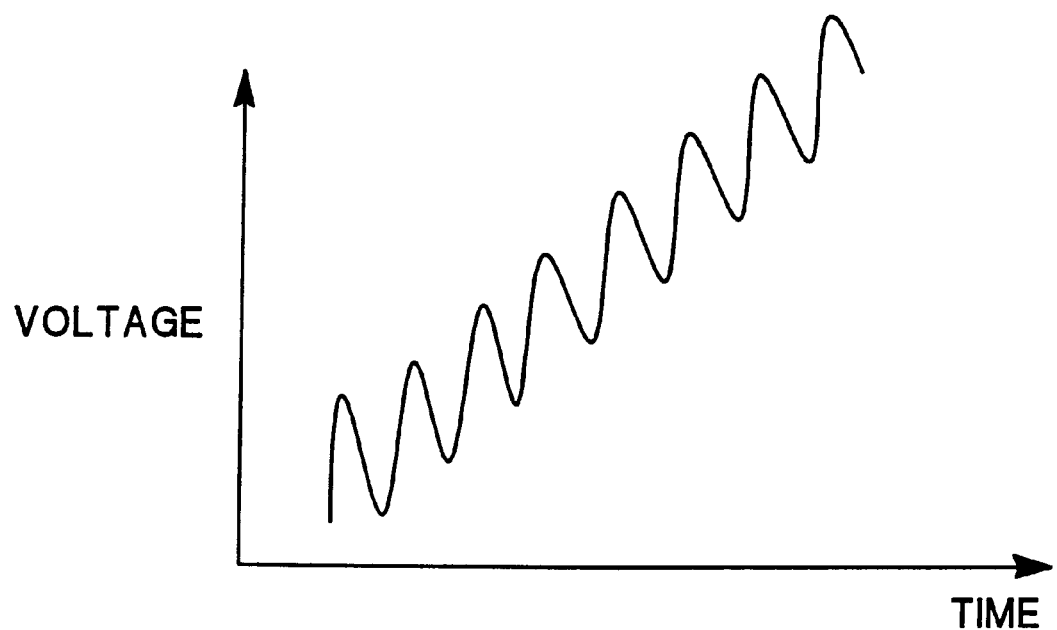
FIG. 18 shows a graphical view of how the proboscis of FIG. 17 can be driven.

Another method for generating the reciprocative movement is by using curved pieces of piezoelectric material (PZT). For example, in a curved piece 154 of PZT as shown in FIG. 17, the magnitude of vibration increases towards the center of the curved piece. Thus, the tube 156 vibrates with a larger magnitude of motion if it is more towards the center of the curve than if it is more on the edge. In this embodiment, the DC (direct current) component of the voltage of the power supply that drives the PZT is slowly ramped up with time (as shown in FIG. 18), causing progressive forward movement of the cutting edge into the tissue, while the AC (alternate current) component causes reciprocative motion for cutting into the tissue. This structure can be used for driving a tube in a proboscis with only one reciprocating tube, e.g., as those described in the above. This mechanism, although suitable for driving a single needle or hollow shaft, can be adapted to drive two or more sections of a proboscis.

Figure 19:
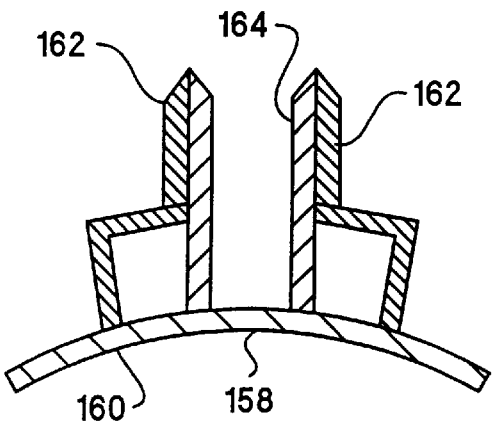
FIG. 19 shows a schematic sectional representation of another embodiment having a curved PZT piece for driving a proboscis.

FIG. 19 shows an embodiment of a curved PZT device which can drive the reciprocative motion of two concentric tubes. The difference in the movement in the longitudinal direction between the two positions 158 and 160 (which are connected respectively to the inner tube 164 and the outer tube 162) on the curved PZT translates into reciprocative relative motion between the inner tube 164 and the outer tube 162. The voltages applied can be adjusted to control the magnitude of the relative reciprocative motion between the tubes 162 and 164.

Figure 20:
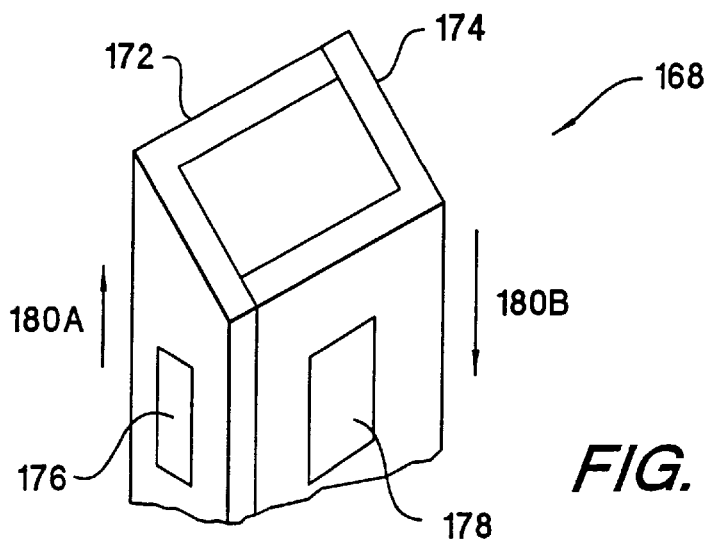
FIG. 20 shows a schematic sectional representation of how a split proboscis can be driven.

In FIG. 20, an embodiment is shown in which two flat PZT pieces 176, 178 are activated out of phase to generate reciprocative movement in a proboscis 168 composed of two longitudinal sections 172, 174. The arrows 180A and 180B shows the direction of movement at a particular instant. The same method generating reciprocative movement can be applied to other embodiments of split proboscis design.

Figure 21:
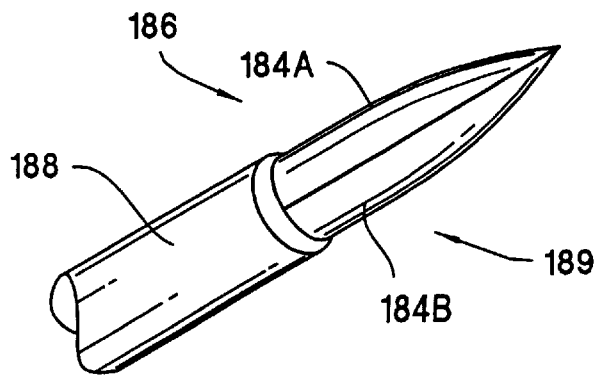
FIG. 21 shows an isometric representation of the distal portion of an embodiment of a proboscis with a split solid shaft of the present invention.

FIG. 21 shows an illustration of a proboscis with a non-hollow, i.e., solid, shaft, which is suitable for creating a puncture hole in a substrate, such as body tissue such as skin, or other soft and resilient materials. In the embodiment of FIG. 21, the reciprocatively moving parts consists of two halves 184A, 184B of a needle 186. A tube 188 encircles the portion of the needle away from the distal portion 189 of the needle 186. The tube 188 allows the needle halves 184A 184B to slide in it and functions to steady the needle halves as they reciprocatively move distally and alternately and slide against each another.

The use of PZT in piezoelectric driving of a proboscis allows the measurement of the mechanical load—measuring the electrical impedance of the PZT drivers. This measurement permits a feedback mechanism to control the mechanical load. The mechanical load can thus be controlled and varied to minimize pain, enhance cutting speed, and control the total penetration depth, or even to stimulate the blood flow through the channel for blood sampling.

Mechanisms for electromechanically, electromagnetically, fluidically, and electrostatically driving reciprocative motion are known in the art. Based on the present disclosure, these mechanisms can be adapted to drive the reciprocative motion of the proboscis sections. Furthermore, the driving mechanism can be controlled such that it stops, or reverses when a certain depth of penetration is reached. For example, an impedance sensor can be used to sense the change in electrical impedance to determine whether the capillary bed has been reached, as described in a copending application(Attorney Docket Number 10971003-1, Inventors: Paul Lum, et al., entitled "APPARATUS AND METHOD FOR PENETRATION WITH SHAFT HAVING A SENSOR FOR SENSING PENETRATION DEPTH") submitted on the same day and assigned to the same assignee as the present application. This copending application also discloses mechanisms for driving a sharp object such as a lancet. Said copending application is incorporated by reference in its entirety herein.

Although the preferred embodiment of the present invention has been described and illustrated in detail, it is to be understood that a person skilled in the art can make modifications within the scope of the invention. For example, a multiple part proboscis according to the present invention may be constructed to be inserted into tissues other than skin, for infusion of fluid rather than withdrawal of fluid in a channel, or for introducing another piece through the proboscis, as in a catheter. In fact, a proboscis according to the present invention can be constructed and inserted into a non-body-tissue material with reduced pressure waves during penetration of the proboscis. Also, a multiple-part pin without a channel can be made for insertion with reduced pain, e.g., for introduction of electrical current, or simply for mechanical stimulation as in acupuncture.

What is claimed is:

1. A multi-shaft apparatus for incising a body tissue, comprising:

two or more incision shafts each having a distal edge, the shafts being non-fixedly associated with one another for periodic motion in translational position or rotational position of at least one of the shafts relative to another of the shafts such that the distal edges thereof can be driven against the body tissue to incise the body tissue.

2. An apparatus according to claim 1 wherein the shafts are aligned in parallel in proximity such that they slide against each other in relative motion.

3. An apparatus according to claim 2 wherein the edges are beveled to each form a sharp edge with a bevel surface and the neighboring bevel surfaces of at least two of the shafts face away from each other.

4. An apparatus according to claim 2 wherein the edges are beveled to form sharp edges with a bevel surface and the neighboring bevel surfaces of at least two of the shafts face each other.

5. An apparatus according to claim 2 wherein the edges are beveled each to form a sharp edge with a bevel surface and the shafts are aligned such that the neighboring bevel surfaces of at least two of the shafts face the same direction.

6. An apparatus according to claim 1 further comprising a driver for driving the shafts for relative motion.

7. An apparatus according to claim 2 wherein the one or more of the shafts moves relative to the other in reciprocating longitudinal action.

8. An apparatus according to claim 2 comprising a tube and wherein one of the shafts comprises at least part of the tube.

9. An apparatus according to claim 2 wherein the shafts are concentric tubes that move in concentric motion.

10. An apparatus according to claim 2 wherein the shafts associate with each other to form a tube each being a part thereof and one shaft moves relative to the other in reciprocating longitudinal action.

11. An apparatus according to claim 1 comprising two shafts aligned in parallel in proximity such that they slide against each other in relative motion.

12. An apparatus according to claim 1 further comprising a piezoelectric driver to drive the relative motion of the shafts.

13. An apparatus according to claim 1 further comprising a tube encircling the shafts and wherein the shafts reciprocatively slide in the tube with each distal edge extending out of the tube to contact the body tissue when cutting.

14. An apparatus according to claim 1 wherein the shafts surround a tubular channel for conducting liquid.

15. An apparatus according to claim 14 wherein the shafts associate with one another to form the tubular channel for conducting liqud.

16. An apparatus according to claim 14 wherein the shafts are concentric tubes where fluid can be conducted in the tubes as a whole.

* * * * *